United States Patent
Saka et al.

(10) Patent No.: US 10,111,421 B2
(45) Date of Patent: Oct. 30, 2018

(54) DISPERSING AGENT FOR AGROCHEMICALS AND FLUID DISPERSION USING THE SAME

(71) Applicant: THE NIPPON SYNTHETIC CHEMICAL INDUSTRY CO., LTD., Osaka (JP)

(72) Inventors: Takahiro Saka, Osaka (JP); Chizuko Furo, Osaka (JP); Shusaku Mandai, Osaka (JP)

(73) Assignee: THE NIPPON SYNTHETIC CHEMICAL INDUSTRY CO., LTD., Osaka (JP)

(*) Notice: Subject to any disclaimer, the term of this patent is extended or adjusted under 35 U.S.C. 154(b) by 0 days.

(21) Appl. No.: 15/428,655

(22) Filed: Feb. 9, 2017

(65) Prior Publication Data

US 2017/0150713 A1    Jun. 1, 2017

Related U.S. Application Data

(63) Continuation of application No. PCT/JP2015/072649, filed on Aug. 10, 2015.

(30) Foreign Application Priority Data

Aug. 20, 2014 (JP) ................. 2014-167461

(51) Int. Cl.
| | |
|---|---|
| *A01N 25/04* | (2006.01) |
| *A01N 25/22* | (2006.01) |
| *A01N 25/30* | (2006.01) |
| *B01F 17/00* | (2006.01) |
| *C08F 116/06* | (2006.01) |
| *C08F 216/06* | (2006.01) |

(52) U.S. Cl.
CPC ............ *A01N 25/04* (2013.01); *A01N 25/22* (2013.01); *A01N 25/30* (2013.01); *B01F 17/0028* (2013.01); *C08F 116/06* (2013.01); *C08F 216/06* (2013.01)

(58) Field of Classification Search
None
See application file for complete search history.

(56) References Cited

U.S. PATENT DOCUMENTS

| | | | | |
|---|---|---|---|---|
| 7,928,166 | B2* | 4/2011 | Shibutani | ............... C08F 8/12 139/420 A |
| 8,722,822 | B2* | 5/2014 | Shibutani | ............... C08J 5/18 526/202 |
| 2010/0120924 | A1 | 5/2010 | Uramatsu et al. | |
| 2010/0234230 | A1* | 9/2010 | Fowler | ............... A01N 25/04 504/289 |
| 2017/0037294 | A1* | 2/2017 | Mandai | ............... C09K 8/24 |

FOREIGN PATENT DOCUMENTS

| | | |
|---|---|---|
| EP | 0794198 A1 | 9/1997 |
| JP | H10-182302 A | 7/1998 |
| JP | 2002-293702 A | 10/2002 |
| JP | 2004-285143 A | 10/2004 |
| JP | 2006124682 A | 5/2006 |
| JP | 2011-63585 A | 3/2011 |
| JP | 2011-168517 A | 9/2011 |
| JP | 2012-236918 A | 12/2012 |
| JP | 2013-209453 A | 10/2013 |
| JP | 2014-111244 A | 6/2014 |

OTHER PUBLICATIONS

International Search Report issued with respect to Application No. PCT/JP2015/072649, dated Oct. 6, 2015.
International Preliminary Report on Patentability issued with respect to Application No. PCT/JP2015/072649, dated Feb. 21, 2017.
European Search Report issued with respect to Application No. 15834136.2, dated Dec. 20, 2017.

* cited by examiner

*Primary Examiner* — Abigail Vanhorn
(74) *Attorney, Agent, or Firm* — Greenblum & Bernstein, P.L.C.

(57) ABSTRACT

Disclosed is a dispersing agent for agrochemicals, said dispersing agent which comprises a modified polyvinyl alcohol-based resin containing a structural unit having a nonionic hydrophilicity group in side chain, and having a saponification degree of 95 mol % or more. The dispersing agent for agrochemicals can provide a dispersion in which a hardly water-soluble agrochemical active ingredient employed for a dispersoid is dispersed in a stable state even in the case where the dispersoid has a relatively large particle size.

14 Claims, No Drawings

DISPERSING AGENT FOR AGROCHEMICALS AND FLUID DISPERSION USING THE SAME

CLAIM FOR PRIORITY

This application is a Continuation of PCT/JP2015/072649 filed Aug. 10, 2015, and claims the priority benefit of Japanese application 2014-167461 filed Aug. 20, 2014, the contents of which are expressly incorporated by reference herein in their entireties.

TECHNICAL FIELD

The present invention relates to a dispersing agent for dispersing a hardly water-soluble agrochemical active ingredient in water, in particular, relates to a dispersing agent for agrochemicals capable of providing an agrochemical fluid dispersion where the agrochemical active ingredient having a relatively large particle diameter as dispersoid can be dispersed stably.

BACKGROUND ART

A fluid dispersion where a hardly water-soluble agrochemical active ingredient is dispersed in water can be applied to spraying and therefore the hardly water-soluble agrochemical active ingredient can spread widely by aerial spraying. In the case that a hardly water-soluble agrochemical active ingredient liquid, its aqueous dispersion may be prepared by diluting the liquid active ingredient with emulsifier such as surfactant. When it comes to a solid and hardly water-soluble agrochemical active ingredient, the solid active ingredient is liquefied by dissolving it in organic solvent and thereafter dissolving the liquefied active ingredient in water in the presence of a water-attracting surfactant, thereby obtaining an aqueous dispersion containing the agrochemical active ingredient. By such a method with assistance of a surfactant or water-soluble polymer and the like, aqueous dispersion of hardly water-soluble agrochemical active ingredients may be prepared, however, the obtained aqueous dispersion has problems associated with storage stability. The problems include a phase separation of the aqueous dispersion while being stored, flocculation of the agrochemical active ingredient, and segmentation of agglomerate of the agrochemical active ingredient.

JP H10-182302A (patent document 1) suggests an aqueous agrochemical composition having a formulation of emulsion or suspension, and comprising an agrochemical active ingredient, protein, polyvinyl alcohol (hereinafter, abbreviated as "PVA"), and surfactant. The patent document 1 also discloses the aqueous agrochemical composition exhibited excellent storing stability for a long term.

The patent document 1 describes that the PVA adopts an unmodified PVA having saponification degree of 90% or less (paragraph 0013), and the surfactant adopts non-ionic, cationic, anionic, or zwitterionic surfactant (paragraph 0015).

JP2002-293702A (patent document 2) discloses aqueous suspension formulation in which dispersoids does not agglomerate while stored, the aqueous suspension formulation being capable of spraying directly to paddy under submerged conditions without dilution. The aqueous suspension formulation is an aqueous suspension where a hardly water-soluble weeding active ingredient is dispersed in water medium in the presence of modified polyvinyl alcohol (modified PVA). As the modified PVA, PVA modified with alkyl group at the terminal thereof, PVA modified with alkyl group in side chain thereof, PVA modified with carboxyl group, PVA modified with cation, PVA modified with silicon-containing group, ethylene sulfonic acid-modified PVA, or PVA modified with acetoacetyl group may be used (paragraph 0011).

Moreover, JP2014-111244A (patent document 3) discloses a polymer-based surfactant utilizing a PVA containing polyoxyalkylene monomer unit. The patent document 3 also discloses the use of the surfactant including emulsifier for agrochemical emulsion or dispersing agent for agrochemical granule (paragraph 0072).

The patent document 3 discloses in example the follows: an aqueous solution using the surfactant had excellent bubble stability; and aqueous dispersion of calcium carbonate particles having an average diameter of 1 to 1.8 μm were stably kept for 30 days of more without separation of the dispersoid phase from water phase.

The paragraph 0021 in the patent document 3 explains that hydrophobic interaction between polyoxyalkylene groups would have been encouraged in polyoxyethylene modified PVA molecules, and thereby demonstrating excellent activity of the surfactant.

PRIOR ART

Patent Document

[Patent document 1] JP H10-182302A

[Patent document 2] JP2002-293702A

[Patent document 3] JP2014-111244A

SUMMARY OF THE INVENTION

Technical Problem to be Solved by the Invention

The agrochemical fluid dispersions disclosed in the documents above-listed aim at storing stability for long term, and therefore adopt agrochemical active ingredient particles having relatively small diameter as the dispersoid. Unduly small dispersoid particles are likely to fly apart, which might cause the agrochemical active ingredient particles to spread in another farm field around the targeted one. Spreading the agrochemicals in non-targeted farm fields would adversely affect growth of crop plant.

On the other hand, dispersoid particles having relatively large diameter tend to lower in dispersion stability of agrochemical active ingredient in fluid dispersion and storing stability of emulsion. For these reasons, there is needs for well-balanced agrochemical fluid dispersion.

Under these circumstances, the present invention has been achieved. The object of the invention is to provide a dispersing agent capable of stably dispersing the dispersoid having a relatively large diameter in a fluid dispersion.

Means for Solving the Problems

A dispersing agent for agrochemicals of the present invention comprises a modified-polyvinyl alcohol-based resin, said modified-polyvinyl alcohol-based resin having 95 mol % or more saponification degree and containing a structural unit represented by the following formula (1) which has a nonionic hydrophilic group in side chain.

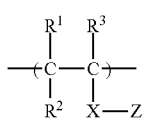

In the formula (1), Z is nonionic hydrophilic group, $R^1$, $R^2$, and $R^3$ each is independently a hydrogen or an alkyl group having 1 to 5 carbon atoms and optionally having a substituent, and X is single bond or a binding chain.

According to the invention, a preferable nonionic hydrophilic group is a hydroxyl-containing group. The hydroxyl-containing group preferably contains one or two primary and/or secondary hydroxyl group(s). Also it is preferable that the structural unit represented by the formula (1) has 8 to 10 in HLB value determined by Davies' method.

In a preferable embodiment of the invention, the modified polyvinyl alcohol-based resin is either side chain 1,2-diol-modified polyvinyl alcohol-based resin or oxyalkylene-modified polyvinyl alcohol-based resin.

The modified polyvinyl alcohol-based resin preferably has a polymerization degree of 100 to 4000. The content of the structural unit of the formula (1) in the modified polyvinyl alcohol-based resin is preferably in the range of 0.1 to 15 mol %.

According to another aspect of the invention, an agrochemical fluid dispersion is included. The agrochemical fluid dispersion comprises a hardly water-soluble agrochemical active ingredient as a dispersoid; a dispersing agent of the invention; and water as a dispersion medium. The agrochemical active ingredient may be liquid.

According to another embodiment of the invention, the agrochemical fluid dispersion may further comprise an organic solvent, and the agrochemical active ingredient is solid at normal temperature in itself but exists as a solution in which the agrochemical active ingredient is dissolved in the organic solvent.

In a preferable agrochemical fluid dispersion of the invention, the dispersoid has an average particle diameter of 10 to 70 μm.

The viscosity of PVA-based resin in the specification is a value measured according to JIS K 6726, with respect to its 4 wt % aqueous solution at 20° C.

The saponification degree is measured according to JIS K 6726.

The particle diameter of dispersoid in fluid dispersion is determined as a median value in volume, which is obtained by the measurement using laser diffraction/scattering type particle diameter distribution analyzer.

HLB (Hydrophilic-lipophilic balance) value based on Davies' method is a value calculated according to the following equation where the contribution is a specific number allotted for a functional group.

HLB value=7+Σ(hydrophilic group contribution)−Σ(lipophilic group contribution)

The contribution of OH group is 1.9, the contribution of —CH$_2$— or CH$_3$— is 0.475, and the contribution of —O— is 1.3.

Effect of the Invention

The dispersing agent for agrochemicals of the invention enables a hardly water soluble agrochemical active ingredient to disperse stably in the form of particle having a relatively large diameter. The resulting dispersion can attain a superior storing stability as well as suppress widely spreading when it is sprayed.

MODES FOR CARRYING OUT THE INVENTION

The following description of the elements is of merely typical embodiments and does not restrict the invention.

The present invention will be described below.

<Dispersing Agent for Agrochemicals>

A dispersing agent for agrochemicals of the invention comprises a modified-polyvinyl alcohol-based resin (modified PVA-based resin) which contains a structural unit represented by the formula (1) having a nonionic hydrophilic group in side chain, and has a saponification degree of 95 mol % or more.

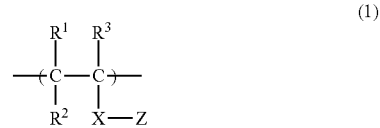

In the formula (1), Z is a nonionic hydrophilic group. Examples of the nonionic hydrophilic group include hydroxyl-containing groups such as hydroxyl-containing alkyl group and oxyalkylene group having hydroxyl at the terminal thereof, amino group, amino group-containing alkyl group, thiol group, thiol-containing alkyl group, and so on. Of these, hydroxyl-containing group is preferred.

The number of hydroxyl groups contained in the hydroxyl-containing group is usually from 1 to 4, preferably 1 to 3, more preferably 1 or 2. As the hydroxyl group contained in the hydroxyl-containing group, a primary and/or secondary hydroxyl group is preferred.

Accordingly, typical examples of the modified PVA-based resin which is modified with hydroxyl-containing group as a preferable nonionic hydrophilic group include side chain 1,2-diol-modified PVA-based resin which contains a structural unit represented by the formula (2) and oxyalkylene-modified PVA-based resin which contains a structural unit represented by the formula (3).

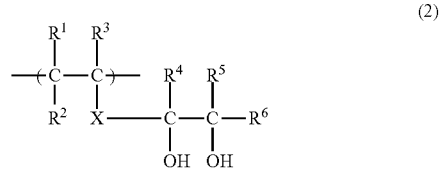

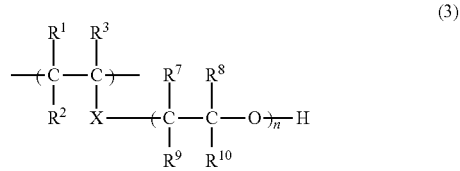

In the formulas (1), (2), and (3), $R^1$, $R^2$, and $R^3$ each is independently hydrogen atom or an alkyl group having from 1 to 5 carbon atoms (e.g. methyl, ethyl, n-propyl, isopropyl, n-butyl, isobutyl, tert-butyl, and pentyl), or an alkyl group having a substituent such as halogen, hydroxyl group, ester group, carboxylic acid group, and sulfonic acid group. Of these, hydrogen atom or an alkyl group having from 1 to 5 carbon atoms is preferred, and hydrogen atom is more preferred.

X is single bond or a binding chain. The binding chain derives from a monomer supplying a structural unit of the formula (1), in other words, the binding chain depends on the unsaturated monomer having Z.

In the formula (2), $R^4$, $R^5$, and $R^6$ each is independently hydrogen atom or an alkyl group having from 1 to 5 carbon atoms (e.g. methyl, ethyl, n-propyl, isopropyl, n-butyl, isobutyl, tert-butyl, and pentyl), or an alkyl group having from 1 to 5 carbon atoms having a substituent such as halogen, hydroxyl group, or ester group. Of these, hydrogen atom or an alkyl group having from 1 to 5 carbon atoms is preferred, and allotting hydrogen atom for all of $R^4$, $R^5$, and $R^6$ is more preferred.

In the formula (3), $R^7$, $R^8$, $R^9$, and $R^{10}$ each is independently hydrogen atom or an alkyl group having from 1 to 5 carbon atoms (e.g. methyl, ethyl, n-propyl, isopropyl, n-butyl, isobutyl, tert-butyl, and pentyl), or an alkyl group having a substituent such as halogen, hydroxyl group, or ester group, and "n" is an integer of 5 to 50. Preferably $R^7$, $R^8$, $R^9$, and $R^{10}$ each is independently hydrogen atom or an alkyl group having from 1 to 5 carbon atoms, and more preferably all of them are hydrogen atoms.

The HLB (hydrophilic-lipophilic balance) value based on Davies' method of the structural unit of the chemical formula (1) is in the range of usually 8 to 10, preferably 8.5 to 9.7. The HLB value based on Davies' method is a value calculated according to the following equation where the contribution is a specific number allotted for the functional group.

HLB value=7+Σ(hydrophilic group contribution)-Σ (lipophilic group contribution)

The contribution of OH group is 1.9, the contribution of —CH$_2$— or CH$_3$— is 0.475, and the contribution of —O— is 1.3.

The unduly low HLB means weak hydrophilicity of hydrophilic group or few hydrophilic groups, in other words, strong lipophilicity or many lipophilic groups. The modified PVA-based resin having unduly low HLB value tends to make larger in the dispersoid particle size of agrochemical active ingredient. If the structural unit has an unduly high HLB value, the structural unit exhibits too strong hydrophilicity, which lowers its affinity to hardly water-soluble agrochemical active ingredient, resulting in lowered storing stability of the fluid dispersion.

The modified PVA-based resin can sustain hydrophilicity based on hydrophilic group in side chain thereof, because the hydrophilic group does not take part in the crystal made of the PVA backbone of the modified PVA-based resin.

The nonionic hydrophilic group-modified PVA-based resin having above-mentioned structure is usually produced by saponifying the copolymer of vinyl ester-based monomer and monomer supplying nonionic hydrophilic group.

Examples of vinyl ester-based monomers include vinyl formate, vinyl acetate, vinyl trifluoroacetate, vinyl propionate, vinyl butyrate, vinyl caprate, vinyl laurate, vinyl versatate, vinyl palmitate, vinyl stearate, vinyl pivalate, and the like. These may be used alone or in a combination thereof. Vinyl acetate is preferably used among them in industry.

The copolymerization method is not limited, any conventionally known method such as bulk polymerization, solution polymerization, suspension polymerization, dispersion polymerization, and emulsion polymerization may be employed, and the solution polymerization may be generally employed. The solvent used in the solution polymerization include lower alcohols such as methanol, ethanol, isopropyl alcohol, n-propanol, and butanol; and ketones such as acetone and methyl ethyl ketone. Of these, methanol is preferably used in industry.

Any conventionally known saponification method may be employed for the saponification method. Specifically, the saponification is conducted in such manner that the obtained copolymer is dissolved in a solvent such as alcohol and saponified with alkali catalyst or acid catalyst.

The typical solvent includes methanol, ethanol, propanol, tert-butanol, and so on, and methanol is particularly preferred. The amount of the copolymer relative to alcohol is appropriately selected depending on viscosity in the reaction system, usually selected form the range of 10 to 60 wt %. Examples of the catalyst to be used for the saponification include alkali catalyst such as sodium hydroxide, potassium hydroxide, sodium methylate, sodium ethylate, potassium methylate, lithium methylate, and the like alkali metal hydroxide or alcoholate; and acid catalyst such as sulfuric acid, hydrochloric acid, nitric acid, methanesulfonic acid, zeolite, and cation exchange resin.

Accordingly, the modified PVA-based resin used in the invention contains vinyl alcohol unit represented by the formula (4), and vinyl ester structural unit represented by the formula (5) corresponding to an unsaponified portion.

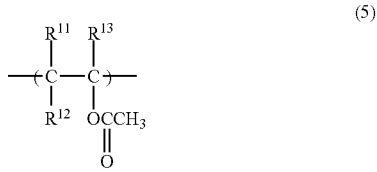

$R^{11}$, $R^{12}$, and $R^{13}$ in the formulas (4) and (5) depend on the kind of vinyl ester used. Each of $R^{11}$, $R^{12}$, and $R^{13}$ is independently hydrogen atom or an alkyl group having carbon atoms of 1 to 18 (preferably 1 to 5, more preferably 1 or 2), and is most preferably hydrogen atom.

The saponification degree of the modified PVA-based resin used in the invention is 95 mol % or more, preferably 96 mol % or more, particularly preferably 97 to 99.9 mol %. Unduly low saponification degree of the modified PVA-based resin means that relatively large amount of hydrophobic groups (vinyl ester structural unit) as the unsaponified unit still remain in the modified PVA. This may lead to readily adsorb to hydrophobic dispersoid and enhance dispersibility of the dispersoid, resulting in lessening the dispersoid particle size.

The polymerization degree of the modified PVA-based resin depends on the kind of modification, and is from usually 100 to 4000, preferably 150 to 2000, more preferably 200 to 1000. Unduly low polymerization degree tends to lower stability of fluid dispersion. Unduly high polymerization tends to increase viscosity of fluid dispersion and results in lowering in spreading property.

The modification degree of the modified PVA-based resin, which corresponds to the content of nonionic hydrophilic group, is in the range of usually 0.1 to 15 mol %, preferably 0.5 to 10 mol %, furthermore preferably 1 to 9 mol %, depending on the kind of modification. The modification of the modified PVA-based resin used in the invention is performed by introducing a structural unit having nonionic hydrophilic group in side chain to the PVA-based resin. The nonionic hydrophilic groups do not take part in the formation of crystal, and therefore would protrude from the agglomerated PVA backbone forming the crystal portion, resulting in readily presenting hydrophilicity to aqueous medium. This would compensate the increase of dispersoid size by use of the PVA-based resin having relatively high saponification degree. As a result, the flocculation of the dispersoid (hardly water-soluble agrochemical active ingredient) would be suppressed and dispersion stability of the resulting dispersion would be improved. Accordingly, a modified PVA-based resin having unduly small modification rate is easily to agglomerate and cause the dispersion using it to become gel easily, which means inferior storing stability of the fluid dispersion. To the contrary, a modified PVA-based resin having unduly large modification rate becomes lower in the rate of the PVA backbone, which reduces dispersibility of agrochemical active ingredient in aqueous medium, as a result, the fluid dispersion exhibits inferior dispersion stability.

Hereinafter, modified PVA-based resins which are modified with hydroxyl-containing group, that is to say, a side chain 1,2-diol-modified PVA-based resin which contains a structural unit represented by the formula (2), and oxyalkylene-modified PVA-based resin which contains a structural unit represented by the formula (3), will be described in detail.

[Side Chain 1,2-diol-modified PVA-Based Resin]

A modified PVA-based resin containing a structural unit represented by the formula (2) is a PVA-based resin containing 1,2-diol in a side chain thereof. Hereinafter, such a modified PVA-based resin is referred to as "side chain 1,2-diol-modified PVA-based resin".

In the case of side chain 1,2-diol-modified PVA-based resin, X is single bond or a binding chain, preferably single bond.

Examples of the binding chain include hydrocarbons such as alkylene, alkenylene, alkynylene, phenylene, and naphthylene (these hydrocarbons may have a substituent such as fluorine, chlorine, or bromine). The binding group also includes —O—, —(CH$_2$O)$_m$—, —(OCH$_2$)$_m$—, —(CH$_2$O)$_m$CH$_2$—, —CO—, —COCO—, —CO(CH$_2$)$_m$CO—, —CO(C$_6$H$_4$)CO—, —S—, —CS—, —SO—, —SO$_2$—, —NR—, —CONR—, —NRCO—, —CSNR—, —NRCS—, —NRNR—, —HPO$_4$—, —Si(OR)$_2$—, —OSi(OR)$_2$—, —OSi(OR)$_2$O—, —Ti(OR)$_2$—, —OTi(OR)$_2$—, —OTi(OR)$_2$O—, —Al(OR)—, —OAl(OR)—, and —OAl(OR)O—, wherein each R is independently a substituent (preferably hydrogen and an alkyl group), and "m" is a natural number. Of these, alkylene group having 6 or less carbon atoms, in particular methylene group or —CH$_2$OCH$_2$— is preferred because of stability in production and use.

In the formula (2), R$^4$, R$^5$, and R$^6$ represent hydrogen atom or an alkyl group having from 1 to 5 carbon atoms (e.g. methyl, ethyl, n-propyl, isopropyl, n-butyl, isobutyl, tert-butyl, and pentyl group), or an alkyl group having a substituent such as halogen, hydroxyl group, or ester group, preferably hydrogen atom.

Accordingly, the most preferable unit for side chain 1,2-diol which is represented by the formula (2) is a unit represented by the formula (2a), which is hydrogen atom allotted for all of R$^1$ through R$^6$ in the formula (2).

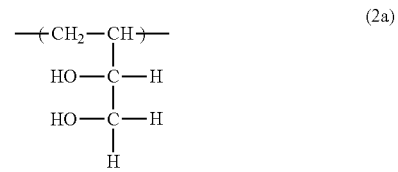

Side chain 1,2-diol-modified PVA-based resin used in the invention may be produced by known methods disclosed in, for example JP2008-163179, paragraphs [0014] through [0037].

Examples of the methods include (i) a method of saponifying a copolymer of vinyl ester-based monomer and a compound represented by the general formula (2-1); (ii) a method of saponifying and decarboxylating the copolymer of vinyl ester-based monomer and a compound represented by the general formula (2-2); and (iii) a method of saponifying and deketalizing the copolymer of vinyl ester-based monomer and a compound represented by the general formula (2-3).

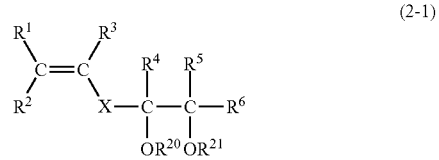

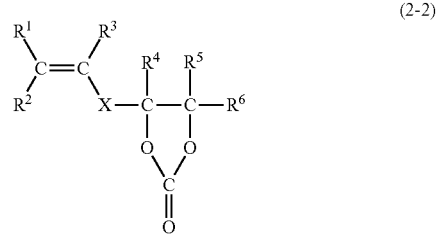

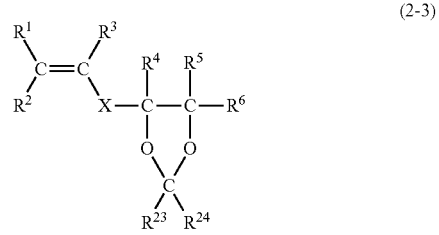

R$^1$, R$^2$, R$^3$, R$^4$, R$^5$, and R$^6$, and X in the formulas (2-1), (2-2), and (2-3) are the same as R', R$^2$, R$^3$, R$^4$, R$^5$, and R$^6$, and X in the formula (2) respectively. R$^{20}$ and R$^{21}$ are independent hydrogen atom or R$^{22}$—CO— wherein R$^{22}$ is an alkyl group (preferably methyl, propyl, butyl, hexyl or octyl), and R$^{23}$ and R$^{24}$ are independently hydrogen or an alkyl group wherein the alkyl group is not limited but preferably includes, for instance, alkyl group having from 1 to 4 carbon atoms such as methyl, ethyl, n-propyl, isopropyl, n-butyl, isobutyl, and tert-butyl.

The alkyl group may have a substituent such as halogen, hydroxyl, or ester, as long as the structural unit of the formula (2) still retain nonionic and have a HLB value in the range specified by the invention.

Examples of the compound represented by the formula (2-1) include, in the case that X is single bond, 3,4-dihydroxy-1-butene, 3,4-diacyloxy-1-butene, 3-acyloxy-4- hydroxy-1-butene, 4-acyloxy-3-hydroxy-1-butene, and 3,4-diacyloxy-2-methyl-1-butene; in the case that X is an alkylene group, 4,5-dihydroxy-1-pentene, 4,5-diacyloxy-1-pentene, 4,5-dihydroxy-3-methyl-1-pentene, 4,5-diacyloxy-3-methyl-1-pentene, 5,6-dihydroxy-1-hexene, and 5,6-diacyloxy-1-hexene; in the case that X is —CH$_2$OCH$_2$— or —OCH$_2$—, glycerin monoallyl ether, 2,3-diacetoxy-1-allyloxypropane, 2-acetoxy-1-allyloxy-3-hydroxy propane, 3-acetoxy-1-allyloxy-2-hydroxy propane, glycerin monovinyl ether, and glycerin monoisopropenyl ether.

Of these, 3,4-diacyloxy-1-butene, which is a compound where all of R$^1$, R$^2$, R$^3$, R$^4$, R$^5$, and R$^6$ are hydrogens, X is single bond, R$^{20}$ and R$^{21}$ are R$^{22}$—CO— wherein R$^{22}$ is an alkyl group, is preferred, and 3,4-diacetoxy-1-butene which is a compound where R$^{22}$ is methyl group is particularly preferred, because of excellent copolymerization reactivity and handleability in industry.

As for the compound represented by the formula (2-2), a compound where all of R$^1$, R$^2$, R$^3$, R$^4$, R$^5$, and R$^6$ are hydrogens, and X is single bond in the formula, i.e. vinyl ethylene carbonate is preferably used because of market availability and excellent copolymerization reactivity.

The decarboxylation may be carried out during its saponification without requiring a specific pretreatment. By the decarboxylation, ethylene carbonate ring is opened and converted to 1,2-diol in side chain. It is possible to accomplish decarboxylation without conducting saponification of vinyl ester under the condition of a high temperature of 50 to 200° C. and a fixed pressure of normal pressure to 1×10$^7$ Pa. In this case, conducting the saponification after the decarboxylation may be allowed.

A preferable compound represented by the formula (2-3), where all of R', R$^2$, R$^3$, R$^4$, R$^5$, and R$^6$ are hydrogens, and R$^{23}$ and R$^{24}$ are methyl group, is 2,2-dimethyl-4-vinyl-1,3-dioxolane because of market availability and excellent copolymerization reactivity.

In the case that saponification reaction is carried out in the presence of alkali catalyst, the deketalization is conducted in water-based solvent (water or a mixed solvent such as water/aceton, water/lower alcohol such as methanol) with use of acid catalyst, thereby providing 1,2-diol in side chain. Examples of the acid catalyst include acetic acid, hydrochloric acid, sulfuric acid, nitric acid, methanesulfonic acid, zeolite, and cation exchange resin. In the case that saponification reaction is carried out in the presence of acid catalyst, deketalization for converting to 1,2-diol in side chain may proceed during saponification without requiring a specific treatment.

The content of the structural unit of the formula (2) (unit having 1,2-diol in side chain) in the side chain 1,2-diol-modified PVA-based resin, which corresponds to the modification rate, is in the range of usually 0.1 to 15 mol %, preferably 2 to 12 mol %, more preferably 4 to 10 mol %. Unduly low modification rate tends to lower stability of the resulting fluid dispersion. Unduly high modification rate would cause a difficulty in the production of side chain 1,2-diol-modified PVA-based resin.

The average polymerization degree of the side chain 1,2-diol-modified PVA-based resin is from usually 100 to 4000, preferably 150 to 2000, more preferably 200 to 800, as a measurement value according to JIS K 6726.

The viscosity of the side chain 1,2-diol-modified PVA-based resin is from usually 1 to 20 mPa·s, preferably 1.5 to 10 mPa·s, more preferably 2 to 10 mPa·s.

In the case that both of the average polymerization degree and the viscosity are too low, PVA backbone forming crystalline structure becomes smaller. This would suppress agglomeration of the PVA backbone which exhibits affinity to hardly water-soluble agrochemical active ingredient, and the resulting fluid dispersion would be impaired in stability of the dispersoid. On the other hand, in the case that both of the average polymerization degree and the viscosity are too high, the resulting fluid dispersion would have higher viscosity, the dispersoid particle size would become larger, or the fluid dispersion would be impaired in dispersion stability and storing stability.

The saponification degree of the side chain 1,2-diol modified PVA-based resin is in the range of usually, 95 mol % or more, preferably 96 to 99.9 mol %, more preferably 97 to 99.8 mol %. In a PVA having around completely saponification degree as the above-mentioned range, the crystallinity made of the PVA backbone is enhanced to become easily agglomeration, while hydrophilic groups in side chain are increased in the PVA-based resin. This could reduce emulsifying ability of the modified PVA, and would allow the dispersoid to increase in its particle diameter as well as to improve its stability in the dispersion based on excellent balance between the main chain and hydrophilic group of the side chain in the modified PVA-based resin.

[Oxyalkylene-Modified PVA-Based Resin]

In the oxyalkylene-modified PVA-based resin containing a structural unit represented by the formula (3), a preferable oxyalkylene as a nonionic hydrophilic group is an oxyalkylene group represented by the formula (3a) from the viewpoint of hydrophilicity, which corresponds to one in the case that R$^7$, R$^8$, R$^9$, and R$^{10}$ each is hydrogen atom in the formula (3).

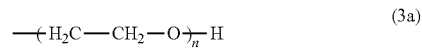

(3a)

In the formula (3a), "n" is usually from 5 to 50, preferably from 8 to 20, more preferably from 8 to 12. If the oxyethylene group is an unduly long chain, the balance between hydrophilicity and hydrophobicity might be lost, and result in lowering dispersion stability. The value of "n" represents average number of oxyethylene groups contained in the oxyethylene-modified PVA-based resin. X is derived from oxyethylene supplying monomer and includes —O—, —CH$_2$—O—, acyloxy group, —CONH—, and so on.

The oxyethylene supplying monomer which introduces oxyethylene group-containing unit represented by the formula (3a) includes polyoxyethylene (meth)acrylate represented by the following formula (3-1); polyoxyethylene (meth)acrylic acid amide represented by the formula (3-2); polyoxyethylene (meth)allyl ether represented by the formula (3-3); and polyoxyethylene vinyl ether represented by the formula (3-4).

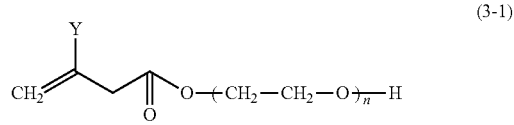

(3-1)

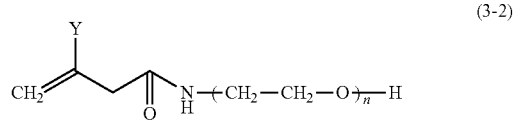

(3-2)

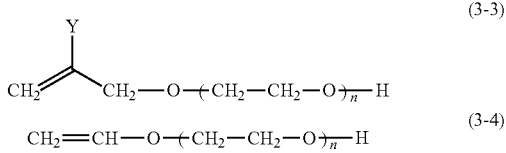

$$CH_2=CH-O-(CH_2-CH_2-O)_n-H \quad (3\text{-}4)$$

In the formulas (3-1), (3-2), (3-3), and (3-4), Y is hydrogen or methyl group, and n is the same as one in the formula (3a).

Of these oxyethylene group-containing monomers, (meth)allyl ether type monomer of the formula (3-3) is preferably used because of easy copolymerization and stability during saponification process.

According to the invention, the oxyethylene modification rate of the oxyethylene-modified PVA-based resin, which corresponds to the content of oxyethylene group-containing structural unit represented by the formula (3a) relative to the PVA-based resin, is in the range of usually 0.1 to 15 mol %, preferably 0.5 to 10 mol %, and particularly preferably 1 to 3 mol %. Unduly low modification rate tends to make it difficult to obtain the effect of the invention. To the contrary, unduly high modification rate could not attain the counter-balanced state between the oxyethylene group-containing structural unit and PVA backbone. This would provide a fluid dispersion with impaired dispersion stability.

According to the invention, the saponification degree of the modified PVA-based resin having nonionic hydrophilic group in side chain is in the range of 95 mol % or more, preferably 96 mol % or more, particularly preferably 97 to 99.9 mol %. The PVA-based resin having around completely saponification degree can become a relatively large particle as a dispersoid particle, and attain a properly balanced state between the PVA backbone and the hydrophilic group in side chain of the PVA, as a result, the fluid dispersion having dispersion stability can be obtained.

The average polymerization degree of the oxyethylene-modified PVA-based resin, which is measured according to JIS K 6726, is in the range of usually 300 to 4000, preferably 400 to 2000, particularly preferably 500 to 1000. Unduly low average polymerization degree tends to lower the stability of the resulting fluid dispersion, whereas unduly high average polymerization degree tends to lower dispersion stability and storing stability due to the fact that the particle size of agrochemical active ingredient becomes excessively large.

The viscosity of the oxyethylene-modified PVA-based resin is in the range of usually 1.5 to 20 mPa·s, preferably 4 to 12 mPa·s, and particularly preferably 5 to 10 mPa·s. Oxyethylene-modified PVA-based resin having too low viscosity is resulted from low polymerization degree of PVA backbone. Such oxyethylene-modified PVA-based resin would not provide a fluid dispersion having an improved stability. Whereas oxyethylene-modified PVA-based resin having too high viscosity has a common drawback of difficult handleability. Since the unduly high viscosity is resulted from that the oxyethylene-modified PVA-based resin has PVA backbone having excessively high average polymerization degree, the size of agrochemical active ingredient as a dispersoid would become excessively large, or the resulting fluid dispersion would have impaired dispersion stability as well as lowered storing stability.

In addition to vinyl ester-based monomer and nonionic hydrophilic group-supplying monomer, another unsaturated monomer may be further copolymerized in the modified PVA-based resin to be used in the invention within the range of not adversely affecting.

Example of the other unsaturated monomers include olefins such as ethylene, propylene, isobutylene, α-octene, α-dodecene, and α-octadecen; unsaturated acids such as acrylic acid, methacrylic acid, crotonic acid, maleic acid, maleic anhydride, itaconic acid, and salt thereof, monoester, or dialkyl ester; nitriles such as acrylonitrile and methacrylonitrile; amides such as diacetone acrylamide, acrylamide, and methacrylamide; olefin sulfonic acids such as ethylene sulfonic acid, allyl sulfonic acid, and methallyl sulfonic acid or salt thereof; alkyl vinyl ethers; vinyl compounds such as dimethyl allyl vinyl ketone, N-vinylpyrrolidone, and vinyl chloride; substituted vinyl acetates such as isopropenyl acetate and 1-methoxyvinyl acetate; vinylidene chloride; 1,4-diacetoxy-2-butene; vinylene carbonate, and acetoacetyl group-containing monomer.

Such another unsaturated monomer may be copolymerized in the content of usually 10 mol % or less, preferably 5 mol % or less, more preferably 1 mol % or less. If the content of the structural unit derived from the other unsaturated monomer is unduly high, the balance between hydrophobicity and hydrophilicity in the modified PVA-based resin would be impaired, which might not attain to a desirous dispersion stability and an intended particle size of dispersoid.

[Agrochemical Active Ingredient]

The agrochemical active ingredient used for the agrochemical fluid dispersion of the invention is a liquid incompatible with water or a solid having very small water solubility.

In the specification, the term of "incompatible with water or having very small water solubility" (hereinafter, which are collectively referred to as "hardly water-soluble") means the case where the dissolution amount is usually from 0.1 to 100 mg, in particular from 1 to 10 mg, per water 100 g at 20° C. When preparing an aqueous dispersion for spraying in which the compound having such a low water solubility is dispersed, dispersion stability is important issue.

Hardly water-soluble agrochemical active ingredients to be used in the invention are shown below:
(Liquid Agrochemical Active Ingredient)
(i) Insecticide For example, carbamate-based compounds such as furathiocarb, carbosulfan, benfuracarb, BPMC, and fenobucarb; synthetic pyrethroids-based compounds such as cyfluthrin, cyhalothrin, fenvalerate, flucythrinate, fluvalinate, silafluofen, cycloprothrin, allethrin, and ethofenprox; and organic phosphorus-based compounds such as EPN, MPP, fenthion, MEP, fenitrothion, propaphos, cyanophos, prothiofos, sulprofos, profenofos, disulfoton, thiometon, PAP, phenthoate, malathion, pyraclofos, BRP, naled, CVP, chlorfenvinphos, pirimiphosmethyl, diazinon, etrimfos, isoxathion, quinalphos, DMTP, and methidathion.
(ii) Bactericide For example, organic phosphorus-based compounds such as edifenphos, and iprobenfos.
(iii) Herbicide For example, acid amide-based compounds such as pretilachlor; carbamate-based compounds such as thiobencarb; organic phosphorus-based compounds such as bensulide; esprocarb; dimethametryn; cyhalofopbutyl and so on.
(Solid Agrochemical Active Ingredient)
(i) Insecticide For example, carbamate-based compounds such as MIPC, isoprocarb, XMC, NAC, carbaryl, bendiocarb, and carbofuran; synthetic pyrehroids-based compounds such as cypermethrin; organic phosphorus-based compound such as cyanofenphos, CVMP, and tetrachlorvinphos; organic chlorine-based compounds such as endosulfan; bensultap; buprofezin; flufenoxuron; diflubenzuron; chlorfluazuron; imidacloprid, and so on.

(ii) Bactericide

For example, N-hetero ring-based ergosterol inhibitors such as triforine; carboxy amide-based compounds such as mepronil, flutoluanil, pencycuron, and oxycarboxin; dicarboxy imide-based compounds such as iprodione, vinclozolin, and procymidone; benzimidazole-based compounds such as benomyl; and polyhaloalkylthio-based compounds such as captan.

Also, organic chlorine-based compounds such as fthalide, TPN, and chlorothalonil; sulfur-based compounds such as zineb and maneb; diclomezin; tricyclazole; probenazole; anilazine; oxolinic acid; ferimzone and so on are included.

(iii) Herbicide

For example, sulfonyl urea-based compounds such as imazosulfuron, bensulfuron-methyl, azimsulfuron, sulfosulfuron, pyrazosulfuron ethyl, and halosulfuron methyl; triazine-based compounds such as simetryn; urea-based compounds such as daimuron; acid amide-based compounds such as propanil, mefenacet, and etobenzanid; carbamate-based compounds such as swep; diazole-based compounds such as oxadiazon and pyrazolate; dinitroaniline-based compounds such as prodiamine; and cafenstrole.

Above-mentioned solid agrochemical active ingredients can be dispersed in the form of solid in water in the presence of the dispersing agent of the invention. According to a preferable embodiment, the solid agrochemical active ingredients are dissolved in organic solvent to form a solution, and the obtained solution is dispersed in water in the presence of the dispersing agent. Examples of the organic solvent include aromatic compounds such as methyl naphthalene, dodecyl naphthalene, tridecylnaphthalene xylene, ethyl benzene, and octadecyl benzene; esters such as aliphatic monocarboxylic acid ester, aliphatic dicarboxylic acid ester, and phthalic acid esters; fatty acid such as cis-9-octadecenoic acid, decanoic acid, and heptanoic acid; animal or vegetable oil such as castor oil, corn oil, soybean oil, sesame oil, canola oil, camellia oil, palm oil, lard, and beef tallow; mineral oil such as paraffin oil, and silicone oil; and other organic solvent having a high boiling point. Of these, aromatic compounds are preferred, and methyl naphthalene is particularly preferred with taking account of flammability.

[Agrochemical Fluid Dispersion]

An agrochemical fluid dispersion of the invention comprises a hardly water-soluble agrochemical active ingredient as a dispersoid; a dispersing agent for agrochemicals of the invention; water as a dispersing medium. The agrochemical fluid dispersion is a fluid dispersion where the agrochemical active ingredient is dispersed in water in the presence of the dispersing agent.

The types of fluid dispersion are as follows: (a) fluid dispersion in which liquid agrochemical active ingredient is dispersed in water; (b) oil in water type dispersion in which droplets made of solution obtained by dissolving solid agrochemical active ingredient in organic solvent are dispersed in water; (c) fluid dispersion in which solid agrochemical active ingredient is dispersed in water.

The (a) type of agrochemical fluid dispersion may be produced by the following methods: (a-i) a method of delivering liquid agrochemical active ingredient by drops into modified PVA-based resin aqueous solution, and dispersing by agitation; (a-ii) a method of adding a lump of modified PVA-based resin aqueous solution and liquid agrochemical active ingredient into water and dispersing by agitation; (a-iii) a method of delivering modified PVA-based resin aqueous solution by drops into liquid agrochemical active ingredient, and dispersing by agitation. Of these methods, the method (a-i) is preferred because of readily attaining stable dispersion.

The (b) type of agrochemical fluid dispersion may be produced by the following methods: (b-i) a method of delivering a solution of agrochemical active ingredient dissolving in organic solvent by drops into modified PVA-based resin aqueous solution, and dispersing by agitation; (b-ii) a method of adding a lump of modified PVA-based resin aqueous solution and organic solvent solution of agrochemical active ingredient into water and dispersing by agitation; (b-iii) a method of delivering modified PVA-based resin aqueous solution by drops into organic solvent solution of agrochemical active ingredient, and dispersing by agitation; and a like method. Of these methods, the method (b-i) is preferred because of readily attaining stable dispersion.

The (c) type of agrochemical fluid dispersion may be produced by the following methods: (c-i) a method of adding solid agrochemical active ingredient into modified PVA-based resin aqueous solution, and dispersing by agitation; (c-ii) a method of feeding a lump of modified PVA-based resin aqueous solution together with solid agrochemical active ingredient, and dispersing by agitation; (c-iii) a method of delivering modified PVA-based resin aqueous solution by drops into solid agrochemical active ingredient, and dispersing by agitation; and a like method. Of these methods, the method (c-i) is preferred because of readily attaining stable dispersion.

The modified PVA-based resin aqueous solution to be used in the above-mentioned methods is prepared by blending a predetermined amount of modified PVA-based resin with water and heating the mixture up to 80 to 90° C. for dissolving the modified PVA-based resin.

The content of the modified PVA-based resin in the agrochemical fluid dispersion of the invention is in the range of usually 0.1 to 20 wt %, preferably 1 to 10 wt %, and particularly preferably 2 to 8 wt %. In the case that the content of the modified PVA-based resin as a dispersing agent is unduly low, dispersion stability of the fluid dispersion tends to be lowered. In the case that the content of the modified PVA-based resin is unduly high, the amount of dispersing agent surrounding dispersoids becomes relatively high, dispersoid particle diameter tends to be decreased.

The content of the agrochemical active ingredient in the agrochemical fluid dispersion of the invention is in the range of usually 1 to 80 wt %, preferably 5 to 60 wt %, and particularly preferably 10 to 50 wt %. The unduly low content of agrochemical active ingredient would become hard to obtain a sufficient effect of agrochemicals in the case of dilution, but unduly high content of agrochemical active ingredient would lower the dispersion stability of the fluid dispersion due to relatively lowered content of dispersing agent. These tendencies vary with types of agrochemical active ingredient.

In the case of using organic solvent for dissolving agrochemical active ingredient, the content of the organic solvent of the agrochemical fluid dispersion is in the range of usually 1 to 80 wt %, preferably 5 to 60 wt %, and particularly preferably 10 to 50 wt %. The amount of the organic solvent is at least necessary for dissolving the agrochemical active ingredient, depending on the type of agrochemical active ingredient. The agrochemical fluid dispersion having unduly large content of the organic solvent would impair the balance given by the dispersing agent in fluid dispersion, as a result, the obtained aqueous dispersion is not suitable for spraying.

The agrochemical fluid dispersion of the invention may further contain thickener, antifoamer, antifreezing agent, and antiseptic agent in addition to the agrochemical active ingredient and dispersing agent.

The agrochemical fluid dispersion of the invention may contain not only one type of agrochemical active ingredient but also the combination of 2 or more types of them, if necessary.

Also, the agrochemical fluid dispersion of the invention may contain not only one kind of modified PVA-based resin as a dispersing agent but also the combination of 2 or more kinds of them. For the combination, used may be 2 or more kinds modified PVA-based resin differing in at least one from type of modifier, modification rate, saponification degree, polymerization degree, and structural unit other than main units in PVA backbone.

The dispersoid particle diameter of the agrochemical active ingredient of the inventive agrochemical fluid dispersion thus produced is in the range of usually 10 to 70 μm, preferably 20 to 60 μm, particularly preferably 30 to 50 μm. Such diameters of the dispersoid is relatively large as compared with the conventional fluid dispersion (emulsion). This can suppress the agrochemical active ingredient flying in all directions when the agrochemical fluid dispersion is sprayed in air. On the other hand, by the presence of the dispersing agent of the invention, agglomeration of dispersoid may be suppressed and storing stability of the dispersion may be sustained regardless of such large dispersoids. Moreover, since the dispersoid of agrochemical active ingredient has a relatively large particle diameter when sprayed in air, the activity loss of the agrochemical active ingredient after sprayed can be reduced. The large sized dispersoid gives a smaller surface area contacting environment as compared with the agrochemical active ingredient in the form of droplet or particle. This means that the former can be reduced in consumption of the active ingredient by the eternal forces, and furthermore the former is readily to encounter insects and kill them effectively.

In the specification, the particle diameter of the agrochemical active ingredient is measured with a laser diffraction/scanning type particle size distribution analyzer. The measurement value is medium diameter based in volume, which is median value corresponding to diameter up to 50% of the accumulative curve based on the whole volume of dispersoid.

The agrochemical fluid dispersion of the invention may be used in unchanged form, or may be diluted with water for use. In the case of dilution, the agrochemical fluid dispersion is diluted up to usually 20 to 2000 times, preferably 100 to 1000 times, particularly preferably 200 to 800 times of volume. The unduly low concentration of the agrochemical fluid dispersion would lower spreading efficiency. To the contrary, the unduly high concentration of the agrochemical fluid dispersion is afraid of excessively being spread.

The amount of the agrochemicals sprayed per crop acreage (unit: 1 hectare) is in the range of usually 10 to 5000 g/ha, preferably 50 to 3000 g/ha, as the amount of agrochemical active ingredient per unit.

Example

The present invention will be described with examples below, but the following examples does not limit the invention unless exceeds the gist of the invention.

The terms “parts” and “%” in the Example is based on weight unless otherwise indicated.

[Dispersing Agent for Agrochemicals]

<Side Chain 1,2-diol-modified PVA>

To a reaction vessel equipped with reflux condenser, dropping funnel, and agitator, vinyl acetate of 10 parts (corresponding to 10% based on its total amount), 3,4-diacetoxy-1-butene of 1.6 parts (corresponding to 10% based on its total amount), and methanol of 30 parts were supplied, wherein the initial amount ratio (S/M) of initial solvent (S) to vinyl acetate monomer (M) was 3.00. Next, azobisisobutyronitrile 0.24 mol % (based on the total amount of vinyl acetate) was added to the vessel. The resulting mixture was heated with agitation under nitrogen gas flow, thereby initiating the polymerization. Thereafter, vinyl acetate of 90 parts and 3,4-diacetoxy-1-butene of 14.4 parts were delivered by drops over 9 hours. The dropping rate per hour was 10% based on the total amounts of monomers used. 11.5 hours later, at the time that the rate of polymerization of the vinyl acetate arrived at 91.7%, the polymerization reaction was terminated by adding 10 ppm of m-dinitrobenzene as a polymerization inhibitor based on the total amount of vinyl acetate. Subsequently, unpolymerized vinyl acetate was removed to the outside the system by giving methanol gas into the system, thereby obtaining methanol solution of the resulting copolymer.

Next, the obtained methanol solution of the copolymer was diluted with methanol to adjust the concentration to 50% and fed to a kneader. The saponification of the copolymer was carried out by adding 2% sodium hydroxide solution (solvent: methanol) to the diluted solution of the copolymer with maintaining the solution temperature at 40° C. The added amount of the sodium hydroxide solution was 12 mmol of sodium hydroxide with respect to 1 mol of the total contents of the vinyl acetate structural unit and 3,4-diacetoxy-1-butene structural unit in the copolymer. Saponified product were separated out with progression of the saponification. The saponified product was finally formed into particles, and thereafter the solution under saponification was filtrated to obtain the particles. The separated particles was washed and dried with hot air dryer, thereby obtaining side chain 1,2-diol-modified PVA.

The obtained side chain 1,2-diol-modified PVA had a saponification degree of 99 mol % and polymerization degree of 300. The saponification degree was determined based on the alkali consumption amount required for hydrolyzing ester part, i.e. unsaponified vinyl acetate structural unit and 3,4-diacetoxy-1-butene structural unit. The modification rate corresponding to the content of side chain 1,2-diol structural unit was 7 mol %, which was determined by the calculation based on the measurement value with $^1$H-NMR (internal standard: tetramethyl silane, solvent: DMSO-d6).

<Polyoxyethylene-Modified PVA>

To a polymerization reactor, 15.0 parts of polyoxyethylene monoallyl ether having oxyethylene group of average chain length (n) of 10, 85 parts of vinyl acetate, and 10.0 parts of methanol were fed. The mixed solution was heated to the state of reflux. After reflux for 30 minutes, azobisisobutyronitrile was added at the amount of 0.08 mol % based on the total amount of vinyl acetate and thereby initiating polymerization. 0.08 mol % of azobisisobutyronitrile based on the total amount of vinyl acetate was added respective 2 hours and 4 hours after the initiation of the polymerization.

About 8 hours after the initiation of the polymerization, 20 parts of methanol for cooling and 0.2 parts of m-dinitrobenzene as an inhibitor were added to the reaction vessel, and thereafter the jacket of the reaction vessel was cooled to terminate the polymerization reaction. As a result, polyoxyethylene group-containing vinyl acetate polymer was obtained. The rate of the polymerization of the polymer was about 95%.

Next, unpolymerized monomer was removed from the polyoxyethylene group-containing vinyl acetate polymer solution, and thereafter the polymer solution was diluted with methanol to adjust the concentration to 40% and then fed to a kneader. In the kneader where the solution temperature was kept at 40° C., the saponification of the polymer solution was carried out by adding 2% sodium hydroxide solution (solvent: methanol). The added amount of the sodium hydroxide was 11 mmol with respect to 1 mol unit of vinyl acetate in the copolymer. The saponification proceeded and the saponified product separated out. At the time that the saponified product formed into particles, the solution after saponification was filtrated to obtain the particles. The separated particles was washed and dried with hot air dryer, thereby obtaining polyoxyethylene-modified PVA. The polyoxyethylene-modified PVA had saponification degree of 99.2 mol %, average polymerization degree of 750, and modification rate corresponding to the content of oxyethylene group-containing unit of 2.0 mol %.

<Acetoacetyl-Modified PVA(A)>

100 parts of PVA having saponification degree of 99 mol %, polymerization degree of 500, and a viscosity of 5 mPa·s (4 wt % aqueous solution) was used. To the kneader in which the PVA was fed in advance, 30 parts of acetic acid was added to make the PVA swollen. After the swollen PVA was heated up to 60° C., 5 parts of diketene was delivered by drops over 5 hours with agitating at rotational frequency of 20 rpm. The saponification reaction continued for further 1 hour and then was terminated. The obtained saponified product was washed with methanol, and dried at 70° C. for 12 hours, resulting in producing acetoacetyl-modified PVA (A). The acetoacetyl-modified PVA(A) had acetoacetylation degree of 5 mol %. The saponification degree and average polymerization degree of the acetoacetyl-modified PVA(A) were unchanged from the PVA used as its raw material.

<Acetoacetyl-Modified PVA(B)>

Acetoacetyl-modified PVA(B) was produced in the same manner except using the PVA having saponification degree of 96 mol %, polymerization degree of 1200, and a viscosity of 14 mPa·s (4 wt % aqueous solution) as the raw material. The obtained acetoacetyl-modified PVA(B) had acetoacetylation degree of 5 mol %, saponification degree of 96 mol %, and polymerization degree of 1200.

<Acetoacetyl-Modified PVA(C)>

The acetoacetyl-modified PVA(C) was produced in the same manner except using PVA having saponification degree of 98 mol %, polymerization degree of 2400, and a viscosity of 52 mPa·s (4 wt % aqueous solution) as the raw material. The obtained acetoacetyl-modified PVA(C) had acetoacetylation degree of 4 mol %, saponification degree of 98 mol %, and polymerization degree of 2400.

[Preparation of Agrochemical Fluid Dispersion]
<Agrochemical Fluid Dispersion Nos. 1 to 7>

The dispersing agent for agrochemicals shown in Table 1 was dissolved with water having a temperature of 80° C. to prepare 7% PVA aqueous solution. 105 parts of the PVA solution was agitated at 2500 rpm with ultra-high speed multi agitation system TK ROBOMIX® (PRIMIX Corporation), and then 45 parts of 1-methyl naphthalene (liquid at normal temperature) as a mimic for an agrochemical active ingredient were delivered by drops over 10 minutes. After the delivery, agitation continued for another 10 minutes, and the agrochemical fluid dispersion was obtained. The obtained agrochemical fluid dispersion was evaluated as described below.

<Agrochemical Fluid Dispersion No. 8>

The agrochemical fluid dispersion No. 8 was prepared in the same manner as the fluid dispersion No. 1 except that anionic surfactant "Emal 20C" (Kao Corporation) was employed for the dispersing agent. The prepared agrochemical fluid dispersion No. 8 was evaluated according to the evaluation method below. The evaluation results are shown in Table 1.

<Agrochemical Fluid Dispersion No. 9>

The agrochemical fluid dispersion No. 9 was prepared in the same manner as the fluid dispersion No. 1 except that nonionic surfactant "Emulgen 103" (Kao Corporation) was employed for the dispersing agent. The prepared agrochemical fluid dispersion No. 9 was evaluated according to the evaluation method below. The evaluation results are shown in Table 1.

[Method for Evaluation and Measurement]
(1) Particle Diameter of Dispersoid 1-methyl naphthalene as the mimic agrochemical active ingredient in the prepared fluid dispersion was measured with respect to median diameter in volume using a laser diffraction/scattering type particle size distribution analyzer LA-950 V2 (HORIBA, Ltd.).

(2) Dispersion Stability

The dispersion stability was evaluated according to the following criteria by visual observation whether or not the sedimentation was occurred in the prepared fluid dispersion containing the mimic agrochemical active ingredient 1 day after being left to stand at room temperature.

○: no sedimentation of 1-methyl naphthalene
  x: occurrence of sedimentation of 1-methyl naphthalene (3) Storing Stability The storing stability was evaluated according to the following criteria by visual observation of fluidity of the prepared fluid dispersion containing the mimic agrochemical active ingredient 2 days after being left to stand at 6° C.

○: fluidity being retained
  x: no fluidity due to gelation (4) HLB Value of Modified PVA For HLB values of the modified PVA, HLB values according to Davies' method of the respective structural units derived from modification were employed.

TABLE 1

| | | Dispersing agent for Agrochemicals | | | | Agrochemical fluid dispersion | | |
|---|---|---|---|---|---|---|---|---|
| No | Kind | Polymerization degree | Saponification degree (mol %) | Modification rate (mol %) | HLB of modification unit | Dispersoid diameter (μm) | Dispersion stability | Storing stability |
| 1 | Side chain 1,2-diol-modified PVA | 300 | 99 | 7 | 8.9 | 36 | ○ | ○ |

TABLE 1-continued

| | | Dispersing agent for Agrochemicals | | | | Agrochemical fluid dispersion | | |
|---|---|---|---|---|---|---|---|---|
| No | Kind | Polymerization degree | Saponification degree (mol %) | Modification rate (mol %) | HLB of modification unit | Dispersoid diameter (μm) | Dispersion stability | Storing stability |
| 2 | Polyoxyethylene (n = 10) · modified PVA | 750 | 99 | 2 | 9.5 | 24 | ◯ | ◯ |
| 3 | Unmodified PVA | 500 | 99 | 0 | — | 33 | ◯ | X |
| 4 | Unmodified PVA | 600 | 88 | 0 | — | 9 | ◯ | ◯ |
| 5 | Acetoacetyl-modified PVA | 500 | 99 | 5 | 7.7 | 26 | X | ◯ |
| 6 | Acetoacetyl-modified PVA | 1200 | 96 | 5 | 7.7 | 10 | X | ◯ |
| 7 | Acetoacetyl-modified PVA | 2400 | 98 | 4 | 7.7 | 6 | X | ◯ |
| 8 | Anioic surfactant | — | — | — | — | 13 | X | ◯ |
| 9 | Nonionic surfactant | — | — | — | — | 22 | X | ◯ |

As from Table 1, in the case that the modified PVA containing 1,2-diol in its side chain or polyoxyethylene chain as a nonionic hydrophilic group and having high saponification degree was used for a dispersing agent, the resulting agrochemical fluid dispersion exhibited superior dispersion stability and storing stability regardless of relatively large mimic agrochemical active ingredient having a particle diameter of 20 to 40 μm (Nos. 1 and 2).

On the other hand, in the case of using unmodified PVA as the dispersing agent (No. 3), the resulting fluid dispersion became gel during being stored although the fluid dispersion was once stably dispersed. The gelation may be caused from high crystallinity due to the unmodified PVA having almost completely saponification degree. In the case of No. 4 where the unmodified PVA was used for a dispersing agent, the fluid dispersion could not attain a large particle as the dispersoid, because a partially saponified PVA used as the unmodified PVA had excellent water-solubility.

In the case of Nos. 5 to 7 where the modified PVAs each containing acetoacetyl group as a nonionic hydrophobic group and having a relatively high saponification degree were used as a dispersing agent, it was difficult to obtain a stable fluid dispersion. Changing particle size of the dispersoid by changing polymerization degree of the PVAs could not achieve the dispersion stability.

In the case of Nos. 8 and 9, where a surfactant was used in place of PVA-based resin, either nonionic surfactant or anionic surfactant could not achieve sufficient dispersion stability.

INDUSTRIAL APPLICABILITY

The dispersing agent for agrochemicals of the invention can disperse a hardly water-soluble agrochemical active ingredient in water in a state that the agrochemical active ingredient has a relatively large particle diameter as dispersoid. This enables the resulting agrochemical fluid dispersion to be sprayed efficiently in the only targeted agricultural field without spreading in all directions. The resulting aqueous dispersion exhibits superior dispersion stability even in water and storing stability regardless of containing a hardly water-soluble agrochemical active ingredient as a dispersoid. Accordingly, the inventive dispersing agent for agrochemicals is useful for dispersing a hardly water-soluble agrochemical active ingredient in water as a dispersion medium.

The invention claimed is:
1. An agrochemical fluid dispersion consisting of
a hardly water-soluble agrochemical active ingredient optionally dissolved in an organic solvent;
water as a dispersion medium; and
a modified-polyvinyl alcohol-based resin,
said modified-polyvinyl alcohol-based resin having 95 mol % or more saponification degree and containing a structural unit represented by the formula (1) which has a nonionic hydrophilic group in side chain;

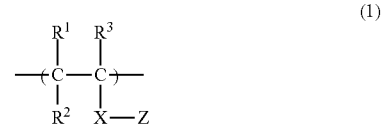

(1)

and
wherein the modified-polyvinyl alcohol-based resin emulsifies the hardly water-soluble agrochemical active ingredient, and
wherein Z is nonionic hydrophilic group, $R^1$, $R^2$, and $R^3$ each is independently a hydrogen or an alkyl group having 1 to 5 carbon atoms and optionally having a substituent, and X is single bond or a binding chain.

2. The agrochemical fluid dispersion according to claim 1, wherein the agrochemical active ingredient is liquid.

3. The agrochemical fluid dispersion according to claim 1, wherein the agrochemical active ingredient is solid at room temperature but exists in a form of a solution in which the agrochemical active ingredient is dissolved in the organic solvent.

4. The agrochemical fluid dispersion according to claim 1, wherein the average particle diameter of the dispersoid is in the range of 10 to 70 μm.

5. The agrochemical fluid dispersion according to claim 1, wherein the nonionic hydrophilic group is a hydroxyl-containing group.

6. The agrochemical fluid dispersion according to claim 1, wherein the hydroxyl-containing group contains one or two primary and/or secondary hydroxyl group(s).

7. The agrochemical fluid dispersion according to claim 1, wherein the structural unit represented by the formula (1) has 8 to 10 in HLB value determined by Davies' method.

8. The agrochemical fluid dispersion according to claim 1, wherein the modified-polyvinyl alcohol is a polyvinyl alcohol-based resin where the structural unit represented by the formula (1) is a unit represented by the formula (2) having 1,2-diol in side chain,

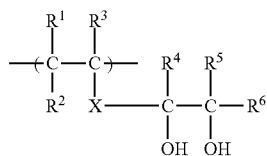
(2)

wherein $R^1$, $R^2$, $R^3$, $R^4$, $R^5$, and $R^6$ each is independently hydrogen or an alkyl group having from 1 to 5 carbon atoms and optionally having a substituent, and X is single bond or a binding chain.

9. The agrochemical fluid dispersion according to claim 1, wherein the modified-polyvinyl alcohol is a polyvinyl alcohol-based resin where the structural unit represented by the formula (1) is a unit represented by the formula (3) having oxyalkylene,

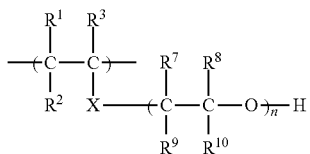
(3)

wherein $R^1$, $R^2$, $R^3$, $R^7$, $R^8$, $R^9$, and $R^{10}$ each is independently is hydrogen or an alkyl group having from 1 to 5 carbon atoms and optionally having a substituent, X is single bond or a binding chain, and n is integer of 5 to 50.

10. The agrochemical fluid dispersion according to claim 1, wherein the modified polyvinyl alcohol-based resin has a polymerization degree of 100 to 4000.

11. The agrochemical fluid dispersion according to claim 1, wherein the content of the structural unit of the formula (1) in the modified polyvinyl alcohol-based resin is in the range of 0.1 to 15 mol %.

12. A method of dispersing a hardly water-soluble agrochemical active ingredient in water consisting of
dispersing the hardly water-soluble agrochemical active ingredient in water in the presence of a modified-polyvinyl alcohol-based resin which has 95 mol % or more saponification degree and contains a structural unit represented by the formula (1) which has a nonionic hydrophilic group in side chain,

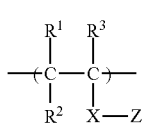
(1)

wherein Z is nonionic hydrophilic group, $R^1$, $R^2$, and $R^3$ each is independently a hydrogen or an alkyl group having 1 to 5 carbon atoms and optionally having a substituent, and X is single bond or a binding chain, and wherein the hardly water-soluble agrochemical active ingredient is liquid.

13. The method of dispersing a hardly water-soluble agrochemical active ingredient in water according to claim 12, wherein the modified-polyvinyl alcohol is a polyvinyl alcohol-based resin where the structural unit represented by the formula (1) is a unit represented by the formula (2) having 1,2-diol in side chain,

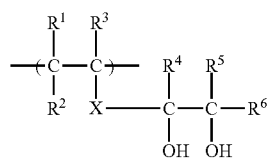
(2)

wherein $R^1$, $R^2$, $R^3$, $R^4$, $R^5$, and $R^6$ each is independently hydrogen or an alkyl group having from 1 to 5 carbon atoms and optionally having a substituent, and X is single bond or a binding chain.

14. The method of dispersing a hardly water-soluble agrochemical active ingredient in water according to claim 12, wherein the modified-polyvinyl alcohol is a polyvinyl alcohol-based resin where the structural unit represented by the formula (1) is a unit represented by the formula (3) having oxyalkylene,

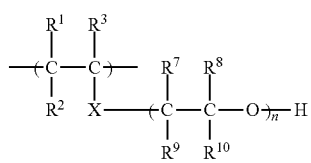
(3)

wherein $R^1$, $R^2$, $R^3$, $R^7$, $R^8$, $R^9$, and $R^{10}$ each is independently is hydrogen or an alkyl group having from 1 to 5 carbon atoms and optionally having a substituent, X is single bond or a binding chain, and n is integer of 5 to 50.

* * * * *